(12) United States Patent
Manz

(10) Patent No.: US 7,671,620 B2
(45) Date of Patent: Mar. 2, 2010

(54) TESTING SYSTEM FOR SOLAR CELLS

(75) Inventor: Dieter Manz, Walddorfhaeslach (DE)

(73) Assignee: Manz Automation AG, Reutlingen (DE)

( * ) Notice: Subject to any disclaimer, the term of this patent is extended or adjusted under 35 U.S.C. 154(b) by 1068 days.

(21) Appl. No.: 11/249,298

(22) Filed: Oct. 13, 2005

(65) Prior Publication Data

US 2006/0103371 A1 May 18, 2006

(30) Foreign Application Priority Data

Oct. 16, 2004 (DE) .................. 10 2004 050 463

(51) Int. Cl.
*G01R 31/26* (2006.01)
(52) U.S. Cl. ............... 324/766; 324/767; 324/158.1
(58) Field of Classification Search ......... 324/754–765, 324/158.1; 414/222.02; 269/21; 279/3; 209/573
See application file for complete search history.

(56) References Cited

U.S. PATENT DOCUMENTS

| | | | |
|---|---|---|---|
| 3,812,947 A | | 5/1974 | Nygaard |
| 5,460,659 A | * | 10/1995 | Krut ............... 136/246 |
| 5,848,868 A | | 12/1998 | Suzuki et al. |
| 6,154,034 A | * | 11/2000 | Lovelady et al. ...... 324/501 |
| 6,183,186 B1 | * | 2/2001 | Howells et al. ...... 414/416.03 |
| 6,265,242 B1 | * | 7/2001 | Komori et al. ......... 438/66 |
| 6,359,212 B1 | * | 3/2002 | Hall et al. ............ 356/239.2 |
| 6,362,020 B1 | * | 3/2002 | Shimoda et al. ........ 438/62 |
| 6,590,408 B1 | * | 7/2003 | Cheng et al. ......... 324/764 |
| 6,657,447 B1 | * | 12/2003 | Parandoosh .......... 324/760 |
| 6,731,127 B2 | * | 5/2004 | Watts .................. 324/765 |
| 6,798,515 B1 | * | 9/2004 | Bachelder et al. ..... 356/397 |
| 6,841,725 B2 | * | 1/2005 | Fortuna ............... 84/477 R |
| 6,944,324 B2 | * | 9/2005 | Tran et al. ............ 382/143 |
| 6,946,858 B2 | * | 9/2005 | Matsuyama ........... 324/752 |

FOREIGN PATENT DOCUMENTS

JP 2001091567 4/2001

\* cited by examiner

*Primary Examiner*—Ha Tran T Nguyen
*Assistant Examiner*—Richard Isla Rodas
(74) *Attorney, Agent, or Firm*—Michael J. Striker

(57) ABSTRACT

A testing system for optical and electrical monitoring of a production quality and/or for determining optical and electrical properties of solar cells, comprising a first conveyor device for conveying the solar cells to a test region, a second conveyor device for moving the solar cells through the test region, a third conveyor device for conveying the solar cells out of the test region, an optical checking device located in the test region for visual checking of the solar, and an electrical checking device also located in the test region for checking electrical functions of the solar cells, the electrical checking device including an illumination device for shining light on light-sensitive surfaces of the solar cells and also including an electrical contacting device for picking up voltages and/or currents and electrical contacts of the solar cells, the first, second and third conveyor devices including a common, linear conveyor belt system which passes through the test region and has a vacuum suction device for holding the solar cells on a surface of a conveyor belt system.

21 Claims, 2 Drawing Sheets

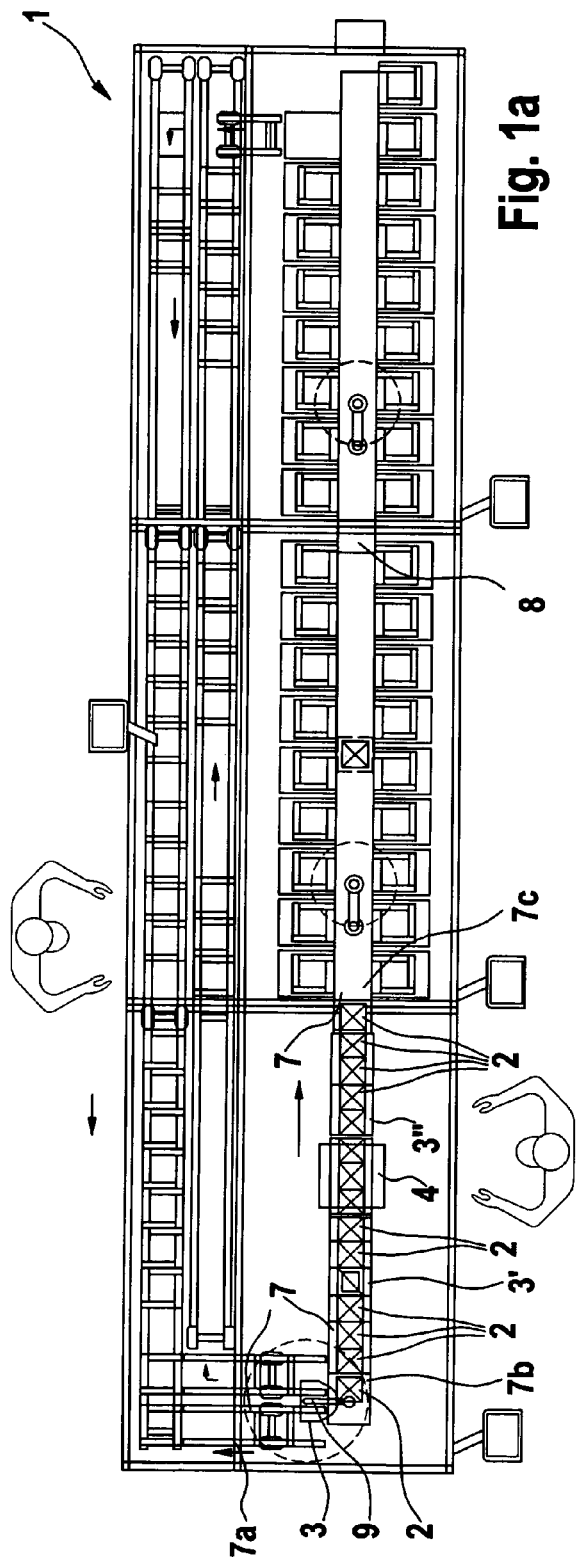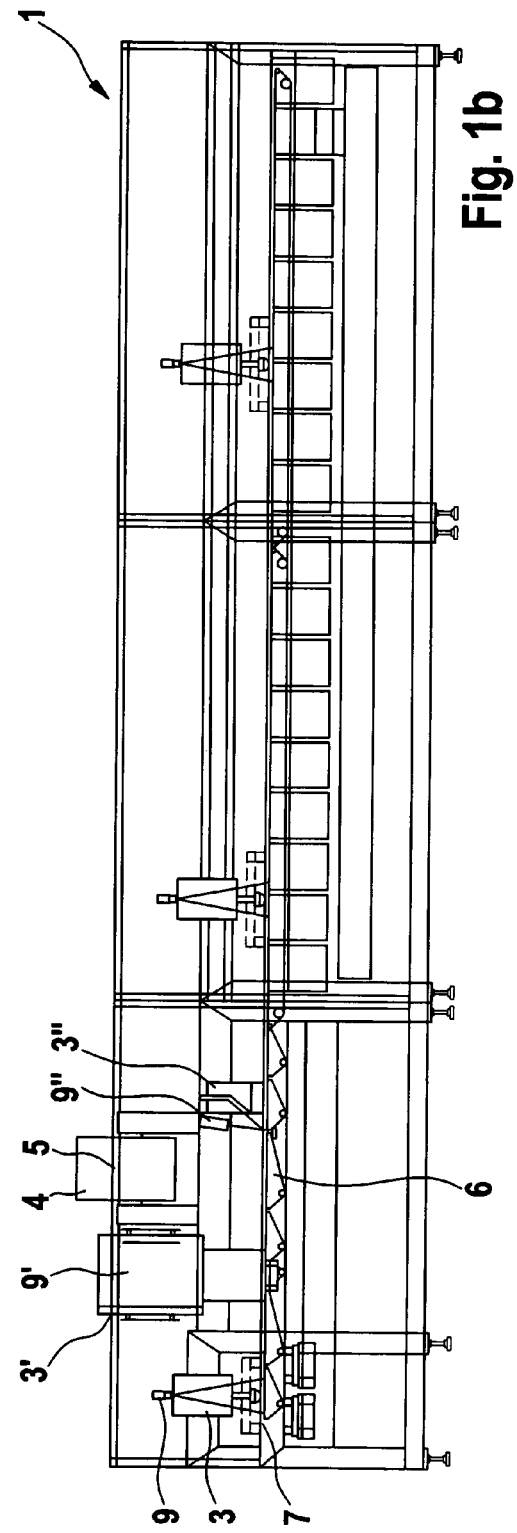

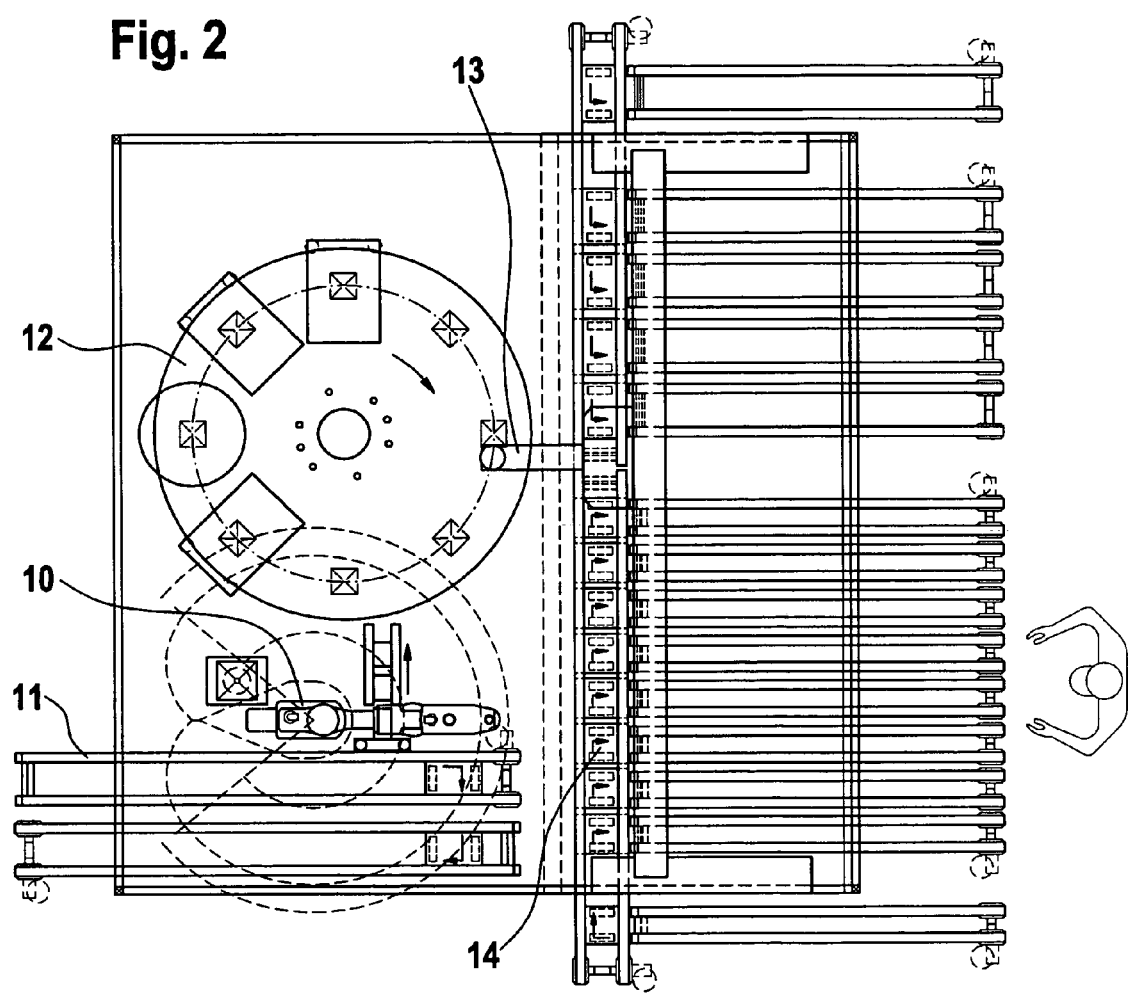

TESTING SYSTEM FOR SOLAR CELLS

BACKGROUND OF THE INVENTION

The invention relates to a testing system for optical and electrical monitoring of the production quality and/or for determining optical and electrical properties of solar cells.

More particularly, it relates to a testing system of the above mentioned type which has a first conveyor device for conveying the solar cells to a test region, a second conveyor device for moving the solar cells through the test region, and a third conveyor device for conveying the solar cells out of the test region, and having an optical checking device, located in the test region, for visual checking of the solar cells, and an electrical checking device, also located in the test region, for checking the electrical functions of the solar cells, the electrical checking device including an illumination device for shining light on the light-sensitive surfaces of the solar cells and also includes an electrical contacting device for picking up voltages and/or currents at electrical contacts of the solar cells.

Such testing systems are typically equipped with the solar cells to be tested via a first conveyor device, in the form of a conveyor belt. In the test region, the solar cells are then taken from the first conveyor device by a robot and placed on an indexing turntable, where they are delivered, in timed increments to the optical checking device for visual checking and to the electrical checking device for function testing. In known testing systems, the optical checking device as a rule includes a area scanning camera, which in the stopped times in the cycle detects the surface of the solar cell to be tested.

Any irregularities are then recognized either by a human or by an assessment computer, and the applicable solar cell is classified as unacceptable or only limitedly acceptable in the cycling of the indexing turntable, and electrical contacting with the solar cell to be examined is then done at a different point in the test region, for checking the electrical functions. In the process, light is shone on the light-sensitive surface of the solar cell, and at corresponding contacts of the solar cell, the current and/or voltages that occur are measured. The electrical checking is typically also done during a stopped time of the indexing turntable.

After the conclusion of the checking operations, the checked solar cell is taken from the indexing turntable again by the same robot arm or a different one and transferred to a third conveyor device, where it is assigned to a defined quality class in accordance with the outcomes of the check and is carried away, usually with a linear belt device. The total cycle time for such a test cycle is between three and five seconds, in testing systems known at present.

However, besides this relatively slow cycle time, the known testing systems also have still other disadvantages:

Because of the use of robot arms and indexing turntables, such devices are relatively expensive and require a relatively large amount of space. When the solar cells to be tested are shifted from the first conveyor device to the second conveyor device and after the conclusion of the checking are shifted from the second conveyor device to the third conveyor device, damage often occurs in supplied or already-checked solar cells, so that on the one hand there are discards and on the other the ensuing sorting by quality classes is not completely reliable.

When the solar cells to be tested are fastened in the holder devices of the indexing turntable, the solar cells usually have a certain waviness, which in turn can impair the precision and conclusiveness of the optical checking.

SUMMARY OF THE INVENTION

Accordingly, it is an object of the present invention to provide a testing system for optical and electrical monitoring of the production quality and/or for determining optical and electrical properties of solar cells, which is a further improvement of the existing testing systems.

More particularly, it is an object of the present invention to improve a testing system of the type defined at the outset, with the simplest possible technological means, in such a way that on the one hand the cycle times for checking the solar cells can be shortened considerably, and on the other the expensive robot for shifting the solar cells among the various conveyor devices and the considerable space required by the indexing turntable can be dispensed with, while at the same time damage upon shifting of the solar cells should be prevented and greater accuracy of the optical checking is attained.

According to the invention, this object is attained in an equally surprisingly simple and surprisingly effective way, in that the first, second and third conveyor devices include a common, linear conveyor belt system, which passes through the test region and has a vacuum suction device for holding the solar cells on a surface of the conveyor belt system. By combining the conveyor devices into one common, linear conveyor belt system, whose individual, linearly conveying conveyor belts may also be located at an angle to one another, both the expensive robot and the indexing turntable that takes up a large amount of space are omitted. It is no longer necessary to shift the solar cells before and after passing through the test region, so that moreover no damage or incorrect sorting into quality classes can occur here. Because of the vacuum suction devices for holding the solar cells, the solar cells are smoothed and are located flat, opposite one another in the test region of the optical checking device, so that the visual checking for mechanical flaws can be done substantially more precisely. Finally, because of the linear guidance, the cycle time in the checking device can also be shortened considerably, making cycle times of less than two seconds, and in continuous operation even checking times on the order of magnitude of one second, attainable.

An embodiment of the testing system of the invention in which the solar cells are located with their light-sensitive surfaces facing upward on the conveyor belt system, and the illumination device of the electrical checking device is mounted above the conveyor belt system in the test region, and the electrical contacting device is mounted below and/or above the conveyor belt system is especially preferred. In this way, the testing system can be constructed in an especially compact, space-saving way in the test region.

An embodiment of the invention in which the conveyor belt system includes at least two parallel belts, extending parallel to the conveying direction, of which at least one has openings that are open toward the belt surface and communicate with the vacuum suction device is also advantageous. Dividing up the conveyor belt into a plurality of parallel belts on the one hand reduces the mass of the belt that has to be moved; on the other, given suitable geometric design, a sufficiently large, secure bearing face for the solar cells to be conveyed is nevertheless furnished.

A refinement of this embodiment in which the parallel belts are spaced apart from one another in a direction crosswise to the conveying direction of the conveyor belt system is especially preferred. In this way, access to the solar cells being conveyed is possible from below.

Quite advantageously, this can be exploited particularly by providing that at least part of the contacting device of the electrical checking device in the test region is located in the gaps between the parallel belts below the conveyor belt system. The electrical contacts of the solar cell to be tested can then be accessed by the electrical contacting device from below, through the gap in the belt.

A refinement of the above-described embodiment, in which the conveyor belt system includes precisely three parallel belts, of which at least the middle one has openings that are open toward the belt surface and communicate with the vacuum suction device, is especially favorable geometrically.

To achieve an absolutely plane location of the solar cell to be tested, all the parallel belts (at least in the test region) may have openings that are open toward the belt surface and communicate with the vacuum suction device.

The precision of the optical measurement can also be further improved by providing that the openings that communicate with the vacuum suction device are distributed uniformly over the surface of the respective parallel belt, which guarantees especially uniform aspiration of the solar cell over its full surface area.

A refinement of the above embodiment in which the parallel belts of the conveyor belt system are driven in common, but for purposes of adjustment may be moved independently of one another in the conveying direction, is also advantageous. As a result, skewed positions of the solar cells to be conveyed can be compensated for or avoided.

A further preferred embodiment of the testing system of the invention is distinguished in that the conveyor belt system includes a plurality of belt segments, following one another in the conveying direction, the length of each of which is a multiple of the length of one solar cell, and in operation, a solar cell arriving at the end of a belt segment is transferred to the beginning of a subsequent belt segment and from the final belt segment is transferred to a further device, in particular a sorter. The individual belt segments can therefore be designed as considerably shorter than one continuous conveyor belt. This also makes it possible to adapt to three-dimensional requirements in an individual application.

In an especially preferred refinement, the belt segments are driven synchronously, in order to accomplish a uniform passage through the test region of the solar cells conveyed.

A refinement of this embodiment in which successive belt segments are spaced apart from one another three-dimensionally in the conveying direction by less than the length of one solar cell is also advantageous. In this way, no separate devices are necessary for transferring the solar cells to be conveyed from one belt to the next.

While in testing systems of the prior art, until now area scanning cameras were used for the optical checking, which survey the surface of the applicable solar cell in stopped times in one cycle, in a preferred embodiment of the testing system of the invention it is provided that the optical checking device includes at least one line scanning camera, which preferably scans the solar cells, moving past it on the conveyor belt system, from above. In this way, the optical checking can be done even continuously, without stopped times of the conveyor device.

It is especially advantageous in this respect if the line scanning camera operates in synchronization with the travel speed of the conveyor belt system, so that an optical monitoring of the entire visible surface of the solar cell to be checked can be assured.

A refinement in which the line scanning camera is located in a gap between successive belt segments is especially particularly preferred. In this way, the optical checking device can be designed in an especially compact, space-saving way.

The cycle time for checking the solar cell can be reduced considerably in embodiments of the invention, if the optical checking device is designed such that the visual checking of the solar cells can be done in operation with the conveyor belt system running, and in particular can be done continuously.

In further embodiments of the testing system of the invention, the electrical checking device may be designed such that the checking of the electrical functions of the solar cells can be done in clocked fashion, in each case in a stopped period between two conveying periods of the conveyor device. Thus cycle times in the range of less than two seconds can be attained for checking the solar cells.

However, an embodiment of the testing system in which the electrical contacting device has contacts that move intermittently with a solar cell traveling past, which contacts, after passing through the portion, automatically return to their outset position, and in which the electrical checking device is designed such that the checking of the electrical functions of the solar cells can be done in operation, with the conveyor belt system running, is very particularly preferred. In this continuous operation, cycle times of approximately one second and less can be attained for checking the solar cells.

Further characteristics and advantages of the invention will become apparent from the ensuing detailed description of exemplary embodiments of the invention in conjunction with the drawings, which show details essential to the invention, and from the claims. The individual characteristics may each be realized individually on their own or together in arbitrary combinations in variants of the invention.

The novel features which are considered as characteristic for the present invention are set forth in particular in the appended claims the invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1a is a schematic plan view from above on an embodiment of the testing system of the invention;

FIG. 1b is a schematic side view of the embodiment of FIG. 1a; and

FIG. 2 shows a testing system of the prior art.

DESCRIPTION OF THE PREFERRED EMBODIMENTS

The embodiment shown in FIGS. 1a and 1b of a testing system 1 of the invention for optical and electrical monitoring of the production quality and/or for determining optical and electrical properties of solar cells 2 includes an optical checking device 3, 3', 3" for inspecting the solar cells 2, which is located in a test region of the testing system 1 and in the present exemplary embodiment, among other things, includes optical monitoring for correctness and completeness of printed conductor elements on the surface of the solar cells 2, checking for correct color and geometry of the solar cells 2, and three-dimensional optical monitoring, for instance for splinters or other foreign bodies located in the printed conductor elements. Also located in the test region of the testing system 1 is an electrical checking device 4 for monitoring the electrical functions of the solar cells 2. It includes an illumination device 5 for shining light on the light-sensitive surfaces of the solar cells 2 and an electrical contacting device 6 for picking up voltages and/or currents at electrical contacts of the solar cells 2. The illumination device 5 is located above and the electrical contacting device 6 is located below and/or above the solar cells 2, traveling past it and to be checked, in the test region.

The solar cells 2 to be monitored are delivered to the test region by a first conveyor device, moved within the test region by a second conveyor device, and finally conveyed out of the test region by a third conveyor device. According to the invention, these three conveyor devices include a common, linear conveyor belt system 7, which in the present exemplary embodiment is constructed of a plurality of synchronously driven belt segments 7a ... 7c in succession in the conveying direction and spaced apart from one another three-dimensionally by less than the length of one solar cell; the length of each of these belt segments amounts to a multiple of that of one solar cell 2, and in operation, a solar cell 2 arriving at the end of one belt segment is transferred to the beginning of a following belt segment and from the last belt segment 7c to a sorter 8 for placing it in various quality classes, based on the measured outcomes of the checking.

The conveyor belt system 7 has a vacuum suction device, not shown in detail in the drawing, for holding the solar cells 2 on a surface of the conveyor belt system. The solar cells 2 to be conveyed are thus held in a way secure against slipping, and moreover any waviness or unevenness of the solar cells 2 that may be present is smoothed, so that particularly their optical monitoring can be done without problems in the optical checking device 3, 3', 3".

The precise construction of the conveyor belts of the conveyor belt system 7 is not shown in detail in the drawing. Preferably, the conveyor belts include three parallel belts, extending parallel to the conveying direction, of which at least the middle one has openings that are open toward the belt surface and communicate with the vacuum suction device. Through the gaps in the belt, the electrical contacting device 6 in particular can grasp the solar cells 2 to be checked, and moving past it, from below. For adjustment purposes, the parallel belts of the conveyor belt system 7 may also be moved independently of one another in the conveying direction.

The optical checking device 3 includes a area scanning camera 9, which is located in a gap between successive belt segments 7a, 7b, and which as a position indicator cooperates with a discharge device, not shown in further detail, for separating the solar cells 2 that are supplied in stacks.

The optical checking device 3' also has a portion (which in other embodiments may also be located in a gap in the belt, and) which includes a line scanning camera 9'. In the next portion of the optical checking device 3" as well, a line scanning camera 9" may be provided for optically scanning the surface of the particularly solar cells 2 moving past it.

Both the optical and the electrical checking of the solar cells 2 can be done in operation with the belt moving, in particular continuously and without stopping the conveying of solar cells. To that end (not shown in further detail in the drawing), the electrical checking device 4 and in particular its contacting device 6 are designed such that checking the electrical functions of the solar cells 2 traveling past is done by means of contacts that in some portions move along with the solar cells and that after passing through the portion automatically return to their outset position. Alternatively, however, the electrical checking can be done in clocked fashion in each case in a stopped period between two conveying periods of the conveyor device.

The testing system of the prior art described at the outset, shown schematically in FIG. 2, includes a robot arm 10, with which solar cells 2 supplied are taken from a first conveyor device 11, designed as a conveyor belt, and are delivered to a second conveyor device, designed as a indexing turntable 12. The indexing turntable 12 conveys the solar cells 2 to be checked in clocked fashion to respective schematically shown optical and electrical measurement stations. After the conclusion of the measurements, the checked solar cell 2 is taken by the robot arm 10 from the applicable station on the indexing turntable 12 and is transferred to a third conveyor device, designed as a transfer belt 13, which transfers the solar cell to a sorter 14, in which, depending on the quality class assigned it after the checking, it is sent for further processing or for shipment.

It will be understood that each of the elements described above, or two or more together, may also find a useful application in other types of constructions differing from the types described above.

While the invention has been illustrated and described as embodied in a testing system for solar cells, it is not intended to be limited to the details shown, since various modifications and structural changes may be made without departing in any way from the spirit of the present invention.

Without further analysis, the foregoing will reveal fully reveal the gist of the present invention that others can, by applying current knowledge, readily adapt it for various applications without omitting features that, from the standpoint of prior art, fairly constitute essential characteristics of the generic or specific aspects of the invention.

What is claimed as new and desired to be protected by Letters Patent is set forth in the appended claims:

1. A testing system for optical and electrical monitoring of a production quality and/or for determining optical and electrical properties of solar cells, comprising a first conveyor device for conveying the solar cells to a test region; a second conveyor device for moving the solar cells through the test region; a third conveyor device for conveying the solar cells out of the test region; an optical checking device located in the test region for visual checking of the solar cells; and an electrical checking device also located in the test region for checking electrical functions of the solar cells, said electrical checking device including an illumination device for shining light on light-sensitive surfaces of the solar cells and also including an electrical contacting device for picking up voltages and/or currents at electrical contacts of the solar cells, said first, second and third conveyor devices including a common, linear conveyor belt system which passes through the test region and has a vacuum suction device for holding the solar cells on a surface of said conveyor belt system.

2. A testing system as defined in claim 1, wherein said conveyor belt system is arranged so that the solar cells are located with their light-sensitive surfaces facing upwards on said conveyor belt system, said illumination device of said electrical checking device being mounted above said conveyor belt system in the test region, and said electrical contacting device being mounted below and/or above said conveyor belt system.

3. A testing system as defined in claim 1, wherein said conveyor belt system includes at least two parallel belts extending parallel to a conveying direction, at least one of said belts having openings that are open toward a belt surface and communicate with said vacuum suction device.

4. A testing system as defined in claim 3, wherein said parallel belts are spaced apart from one another in a direction crosswise to a conveying direction of said conveyor belt system.

5. A testing system as defined in claim 3, wherein at least a part of said contacting device of said electrical checking device in the test region is located in gaps between said parallel belts below said conveyor belt system.

6. A testing system as defined in claim 3, wherein said conveyor belt system includes a third parallel belt, so that said conveyor belt system has three said parallel belts, at least a middle one of said three parallel belts having openings that are open toward the belt surface and communicate with said vacuum suction device.

7. A testing system as defined in claim 3, wherein parallel belts have openings that are open toward the belt surface and communicate with said vacuum suction device.

8. A testing system as defined in claim 7, wherein said openings that communicate with said vacuum suction device are distributed uniformly over a surface of a respective one of said belts.

9. A testing system as defined in claim 3, wherein said parallel belts of said conveyor belt system are driven in common, but for purposes of adjustment are movable independently of one another in a conveying direction.

10. A testing system as defined in claim 1, wherein said conveyor belt system includes a plurality of belt segments in succession in a conveying direction, each of said belt segments having a length which is a multiple of a length of one solar cell, and in operation a solar cell arriving at an end of a respective one of said belt segments is transferred to a beginning of a subsequent one of said belt segments and from a final one of said belt segments is transferred to a further device.

11. A testing system as defined in claim 10, wherein said further device is formed as a sorter.

12. A testing system as defined in claim 10, wherein said belt segments are driven synchronously.

13. A testing system as defined in claim 10, wherein said successive belt segments are spaced apart from one another three-dimensionally in the conveying direction by less than a length of one solar cell.

14. A testing system as defined in claim 1, wherein said optical checking device includes at least one line scanning camera.

15. A testing system as defined in claim 13, wherein said at least one line scanning camera scans the solar cells moving past it on said conveyor belt system from above.

16. A testing system as defined in claim 14, wherein said line scanning camera operates in synchronization with a travel speed of said conveyor belt system.

17. A testing system as defined in claim 14, wherein said line scanning camera is located in a gap between successive belt segments of said conveyor belt system.

18. A testing system as defined in claim 1, wherein said optical checking device is configured so that the visual checking of the solar cells is done in operation with said conveyor belt system running.

19. A testing system as defined in claim 18, wherein said optical checking device is configured so that the visual checking of the solar cells is done in operation continuously with said conveyor belt system running.

20. A testing system as defined in claim 1, wherein said electrical checking device is configured so that the checking of the electrical functions of the solar cells is doable in clocked fashion, in each case in a stopped period between two conveying periods of said conveyor device.

21. A testing system as defined in claim 1, wherein said electrical contacting device has contacts that move intermittently with a solar cell traveling past, said contacts, after passing through a portion, automatically returning to their outset position, said electrical checking device being configured so that the checking of the electrical functions of the solar cells is doable in operation with said conveyor belt system running.

* * * * *